US010830779B2

(12) United States Patent
Martinez Martinez et al.

(10) Patent No.: US 10,830,779 B2
(45) Date of Patent: Nov. 10, 2020

(54) LATERAL FLOW IMMUNOASSAYS FOR THE DETECTION OF ANTIBODIES AGAINST BIOLOGICAL DRUGS

(71) Applicant: PROGENIKA BIOPHARMA, S.A., Derio (ES)

(72) Inventors: Antonio Martinez Martinez, Derio (ES); Daniel Nagore Casas, Derio (ES); Alberto Monasterio Asteinza, Derio (ES); Nerea Torres Antúnez, Derio (ES)

(73) Assignee: PROGENIKA BIOPHARMA, S.A., Derio (ES)

( * ) Notice: Subject to any disclaimer, the term of this patent is extended or adjusted under 35 U.S.C. 154(b) by 559 days.

(21) Appl. No.: 15/502,733

(22) PCT Filed: Jul. 27, 2015

(86) PCT No.: PCT/IB2015/055675
§ 371 (c)(1),
(2) Date: Feb. 8, 2017

(87) PCT Pub. No.: WO2016/020790
PCT Pub. Date: Feb. 11, 2016

(65) Prior Publication Data
US 2017/0234896 A1 Aug. 17, 2017

(51) Int. Cl.
*G01N 33/558* (2006.01)
*G01N 33/94* (2006.01)
(Continued)

(52) U.S. Cl.
CPC ....... *G01N 33/94* (2013.01); *G01N 33/54306* (2013.01); *G01N 33/558* (2013.01); *G01N 33/686* (2013.01)

(58) Field of Classification Search
USPC ..... 422/400, 401, 420, 425, 430; 435/287.7, 435/287.9, 970, 805, 810; 436/169, 514,
(Continued)

(56) References Cited

U.S. PATENT DOCUMENTS

| 5,252,496 A | * | 10/1993 | Kang ............... G01N 33/54366 436/529 |
| 7,527,765 B2 | * | 5/2009 | Royds ............. G01N 33/54366 422/68.1 |

(Continued)

FOREIGN PATENT DOCUMENTS

| WO | WO 2011/005357 A2 | 1/2011 |
| WO | WO 2011/135024 A1 | 11/2011 |
| WO | WO 2006/119160 A2 | 11/2016 |

OTHER PUBLICATIONS

AbD Serotec, A Bio-Rad Company, Effective Tools for Drug Monitoring Assays, pp. 1-2, Aug. 8, 2007.
(Continued)

*Primary Examiner* — Christopher L Chin
(74) *Attorney, Agent, or Firm* — Knobbe, Martens, Olson & Bear, LLP

(57) ABSTRACT

A lateral flow immunoassay for the detection of anti-drug antibodies against a biological drug includes a membrane having a capture area, a sample application area, a flow path from the sample application area to the capture area, and a conjugate area located in the flow path. The conjugate area has said biological drug detectably labeled and the capture area has said biological drug immobilized thereto.

15 Claims, 6 Drawing Sheets

(51) Int. Cl.
  *G01N 33/543* (2006.01)
  *G01N 33/68* (2006.01)
(58) Field of Classification Search
  USPC .......................................... 436/518, 530, 810
  See application file for complete search history.

(56) References Cited

U.S. PATENT DOCUMENTS

| | | | | |
|---|---|---|---|---|
| 8,399,261 B2* | 3/2013 | Kabir | ................. | G01N 31/22 422/420 |
| 2001/0026944 A1* | 10/2001 | Chung | ................. | G01N 33/558 436/518 |
| 2008/0233659 A1* | 9/2008 | Kasinrerk | ............ | G01N 33/721 436/501 |
| 2009/0061466 A1* | 3/2009 | Hoesel | ............. | G01N 33/54353 435/7.92 |
| 2015/0226758 A1* | 8/2015 | Grabert | .............. | G01N 33/5306 506/9 |
| 2015/0285815 A1* | 10/2015 | Parussini | ............. | G01N 33/564 506/9 |

OTHER PUBLICATIONS

Corstjens et al., A rapid assay for on-site monitoring of infliximab trough levels: a feasibility study, Analytical and Bioanalytical Chemistry, vol. 405, No. 23, pp. 7367-7375, Jul. 9, 2013.
Nelson et al., Biological Drugs: Drugs of the Future, Consumer Health Information, pp. 1-2, Jan. 1, 2008.
Pan et al., Comparison of the NIDS® rapid assay with ELISA methods in immunogenicity testing of two biotherapeutics, Journal of Pharmacological and Toxicological Methods, vol. 63, No. 2, pp. 150-159, Sep. 13, 2010.
Ruiz-Argüello et al., Comparison study of two commercially available methods for the determination of infliximab, adalimumab, etanercept and anti-drug antibody levels, Clinical Chemistry and Laboratory Medicine, vol. 51, No. 12, pp. e287-e289, Dec. 1, 2013.
Tornetta et al., Isolation of human anti-idiotypic antibodies by phage display for clinical immune response assays, Journal of Immunological Methods, vol. 328, No. 1-2, pp. 34-44, Oct. 30, 2007.
Wang et al., A rapid immunochromatographic test strip for detecting rabies virus antibody, Journal of Virological Methods, vol. 170, No. 1-2, pp. 80-85, Dec. 1, 2010.
International Search Report and Written Opinion, dated Oct. 23, 2015, in International Application No. PCT/IB2015/055675.
International Preliminary Report on Patentability, dated Jul. 22, 2016, in International Application No. PCT/IB2015/055675.
Bartelds, G.M., et al., Development of Antidrug Antibodies Against Adalimumab and Association with Disease Activity and Treatment Failure During Long-Term Follow-Up, JAMA, vol. 305, No. 14, pp. 1460-1468, 2011.
Biagini, R, et al., Rapid, Sensitive, and Specific Lateral-Flow Immunochromatographic Devise to Measure Anti-Anthrax Protective Antigen Immunoglobulin G in Serum and Whole Blood, Clinical and Vaccine Immunology, vol. 13, No. 5, pp. 541-546, 2006.
Brown, M., Antibodies: Key to a Robust Lateral Flow Immunoassay, Lateral Flow Immunoassay, pp. 59-61, R.C. Wong, H.Y. Tse (eds.), Humana Press, New York, 2009.
Lisa—Tracker Premium Infliximab, Product Insert, LT1001, pp. 10-18, May 2012.
Notice of Opposition, dated Jan. 2, 2018, in European Patent No. EP3092497.

O'Farrell, B., Evaluation in Lateral Flow-Base Immunoassay Systems, Lateral Flow Immunoassay, pp. 1-5, R.C. Wong, H.Y. Tse (eds.), Humana Press, New York, 2009.
Pan, J., et al., Comparison of the NIDS® rapid assay with ELISA methods in immunogenicity testing of two biotherapeutics, Journal of Pharmacological and Toxicological Methods, vol. 63, pp. 150-159, 2011.
Xiang, T., et al., A Novel Double Antibody Sandwich-Lateral Flow Immunoassay for the Rapid and Simple Detection of Hepatitis C Virus, International Journal of Molecular Medicine, vol. 30, pp. 1041-1047, 2012.
Detection of Infliximab and anti-Infliximab antibodies with ELISA or high-Performance Liquid Chromatography, Apr. 2014.
Promonitor—ANTI-IFX Ref. 5070230000, Nov. 2015.
Maser, et al., Association of Trough Serum Infliximab to Clinical Outcome After Scheduled Maintenance Treatment for Crohn's Disease, Clinical Gastroenterology and Hepatology, vol. 4, pp. 1248-1254, 2006.
Bartelds et al., Clinical Reponse to Adalimumab: Relationship to Anti-Adalimumab Antibodies and Serum Adalimumab Concentrations in Rheumatoid Arthritis, Annals of the Rheumatic Diseases vol. 66, No. 7, pp. 921-926, 2007.
Llinares-Tello et al., Analytical and Clinical Evaluation of a New Immunoassay for Therapeutic Drug Monitoring of Infliximab and Adalimumab. Clinical Chemistry and Laboratory Medicine, vol. 50, No. 10, pp. 1845-1847, 2012.
Ruiz-Arguello et al., Comparison Study of Two Commercially Available Methods for the Determination of Infliximab, Adalimumab, Etanercept and Anti-Drug Antibody Levels, Clinical Chemistry and Laboratory Medicine, vol. 51, No. 12, pp. e287-e289, 2013.
Gerbers, et al., Development of enhanced Lateral Flow Test Devices for Point-of-Care Diagnostics, Open Access Master's These, Paper 123.
BioThrax (Anthrax Vaccine absorbed), Package insert and Information for Patients, https://www.fda.gov/media/71954/download.
Study Record Detail NCT01491607, https://clinicaltrials.gov/ct2/show/NCT01491607 Veroffentlicht Am 28. Nov. 2013, Zuletztz Aufgerufen am 12. Nov. 2019.
Powell et al., Multiple Asparagine Deamidation of Bacillus anthracis Protective Antigen Causes Charge Isoforms Whose Complexity Correlates With Reduced Biological Activity, Proteins: Structure, Function, and Bioinformatics, vol. 68, pp. 458-479, 2007.
Parolo et al., Enhanced Lateral Flow Immunoassay Using Gold Nanoparticles Loaded With Enzymes, Biosensors and Bioelectronics, vol. 40, No. 1, pp. 412-416, 2013.
Mao et al., Rapid Quantitative Immochromatographic Strip for Multiple Proteins Tests, Sensors and Actucators B., vol. 186, pp. 315-320, 2013.
The Immunoassay Handbook, Ed. D. Wild, $4^{th}$ ed., Elsevier, pp. 279, 2013.
Interchim Innovations, Tagged antibodies (Biotin label, and more labels & tags); Downloaded Mar. 26, 2020.
Dundas et al., Streptavidin—biotin technology: improvements and innovations in chemical and biological applications, Applied Microbiology and Biotechnology, vol. 97, No. 21, 2013.
Opponent's Brief dated Dec. 20, 2018 in European Application No. EP3092497B1.
Response to the Preliminary Opinion dated Dec. 20, 2018 in European Application No. EP3092497B1.
Additional arguments submitted by the Opponent dated Feb. 8, 2019 in European Application No. EP3092497B1.
Opponent's Response dated Dec. 5, 2019 in European Application No. EP3092497B1.
Response dated Feb. 27, 2020 to Appeal proceedings in the opposition in European Application No. EP3092497B1.

* cited by examiner (A)

(B)

(A)

(B)

(A)

CL
TL (B)

(C)

LATERAL FLOW IMMUNOASSAYS FOR THE DETECTION OF ANTIBODIES AGAINST BIOLOGICAL DRUGS

PRIORITY AND CROSS REFERENCE TO REPLATED APPLICATIONS

This application is the U.S. National Stage Application under 35 U.S.C. § 371 of International Application No. PCT/IB2015/055675, filed Jul. 27, 2015, designating the U.S. and published as WO 2016/020790 A1 on Feb. 11, 2016, which claims the benefit of Spanish Patent Application No. 201431216, filed Aug. 8, 2014. Any and all applications for which a foreign or a domestic priority is claimed is/are identified in the Application Data Sheet filed herewith and is/are hereby incorporated by reference in their entirety under 37 C.F.R. § 1.57.

BACKGROUND

The present invention relates to the in vitro diagnostic field. More precisely, the present invention relates to lateral flow immunoassays for the detection of antibodies against biological drugs and methods and uses thereof.

SUMMARY

The present invention allows a rapid, almost instantaneous, on-site qualitative detection of ADA in patients that would simplify and accelerate clinical decision in the course of biological therapy in autoimmune and inflammatory disease giving the possibility to take decisions on the next dose of biological drug to administer on the basis of the results of the assay.

BRIEF DESCRIPTION OF THE DRAWINGS

In FIG. 5(B) the x-axis refers to U of ADA against IFX/ml of serum and the y-axis refers to Rann score. In FIG. 5(C) the x-axis refers to U of ADA against IFX/ml of serum and the y-axis refers to Camag data. From right to left in FIGS. 5(A), (B) and (C), the concentration of ADA in the samples applied to the strips is: 506 U/ml, 253 U/ml, 127 U/ml, 63 U/ml, 32 U/ml, 16 U/ml and 0 U/ml.

FIGS. 6(B) and (C) also show the results obtained for the same serial dilution performed only with serum. In FIG. 6(B) the x-axis refers to U of ADA against IFX/ml of serum or spiked whole blood and the y-axis refers to Rann score. In FIG. 6(C) the x-axis refers to U of ADA against IFX/ml of serum or spiked whole blood and the y-axis refers to Camag data. From right to left in FIGS. 6(A), (B) and (C), the concentration of ADA in the samples applied to the strips is: 384 U/ml, 192 U/ml, 96 U/ml, 48 U/ml, 24 U/ml, 12 U/ml and 0 U/ml. In addition, in FIGS. 6(B) and (C), white bars refer to serum samples and bars with diagonal lines refer to whole blood samples (both spiked or not with positive serum).

DETAILED DESCRIPTION

Figure 1:
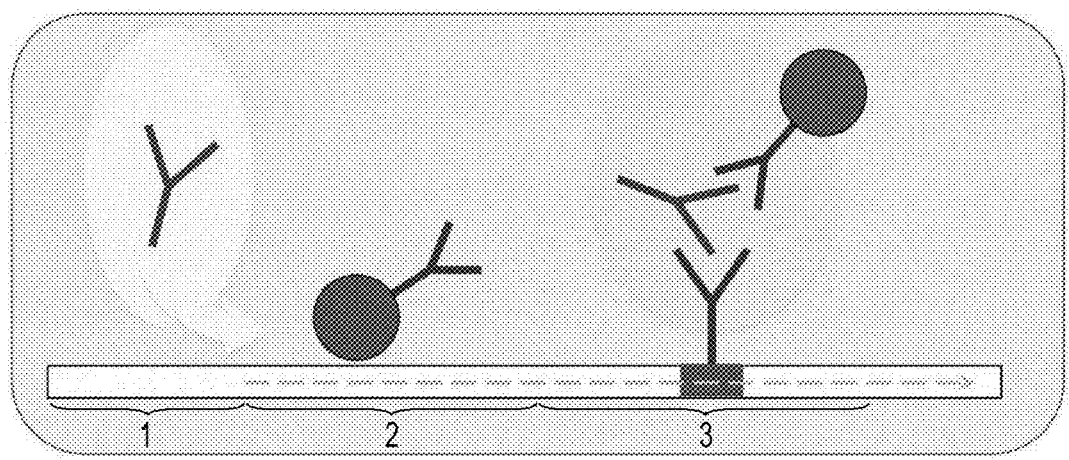
FIG. 1 shows an schematic view of the lateral flow immunoassay of the present invention with the at least three zones that the membrane or test strip comprises: a first zone called sample pad where the sample to be tested for the presence of ADA is applied (1); a second zone called conjugate area wherein biological drug conjugated to a label is placed (2); and a third zone where the biological drug is immobilized in the membrane or test strip to act as capture reagent (3).
Figure 2:
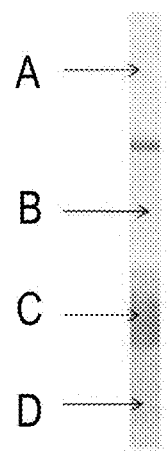
FIG. 2 shows an exemplary structure of a lateral flow immunoassay of the present invention where A is the distal absorbent pad, B is the nitrocellulose membrane, C is the conjugate pad and D is the blood separation pad.

The last decade has seen a revolution in the treatment of patients with various immunoinflammatory diseases, for example arthritic diseases (for example, rheumatoid arthritis, ankylosing spondylitis), inflammatory bowel diseases (for example, Crohn's disease, ulcerative colitis), skin diseases (for example, psoriasis, hidradenitis suppurativa), non-infectious diseases of the eye (for example, diabetic macular edema, age-related macular degeneration) and refractory asthma (Furst, D E., et al., Arthritis Care Res, 2011, 63, 856-864; Jemec, G B., Br J Dermatol, 2013, 168, 233). Proinflammatory cytokine Tumor Necrosis Factor-alpha (TNF-α) plays a pivotal role in the pathogenesis of these and other inflammatory and autoimmune disorders (Kopylov, U., et al., Alimentary pharmacology & therapeutics, 2011, 33, 349-357).

In recent years, biological drugs (for example, monoclonal antibodies) have emerged as a promising alternative and are expected to gain importance in the coming years (Nelson, T. and Smith, D. L., Consumer Health Information Corporation, 2008, 1-2). Since the approval of the first therapeutic monoclonal antibody against TNF-α fifteen years ago, the use of biological drugs in clinical practice has grown constantly. The treatment of inflammatory and autoimmune diseases that are usually refractory to conventional treatments has improved considerably since combination regimes of these new biological drugs and the classical disease modifying anti-rheumatic drugs (DMARDS) were introduced (Krieckaert, C L., et al., Arthritis Res Ther, 2010, 12, 217).

Infliximab (IFX) is a chimeric mouse-human monoclonal antibody that targets or is directed against TNF-α.

Moreover, IFX was the first antibody-based therapy to be accepted for the treatment of patients with rheumatoid arthritis (RA). Nowadays, its use has become more generalized and it is being administered to a growing number of patients at an early stage of disease. Some patients initially respond to treatment but subsequently their responsiveness decreases (Bendtzen, K., et al., Arthritis Rheum, 2011, 63, 867-870). One of the alleged reasons for this phenomenon is immunogenicity associated with the drug itself, i.e. immunological response of the patient against the drug.

Biological drugs can induce the formation of neutralizing antibodies (Vincent, F B. et al., Ann Rheum Dis, 2013, 72, 165-178), resulting in a loss or reduction of the effectiveness of the treatment and the appearance of side effects such as infusion-related reactions (Korswagen, L A., et al., Arthritis Rheum, 2011, 63, 877-883). It has been described that there is a significant correlation between serum biological drug levels (DL), levels of anti-drug antibodies (LADA) and the clinical response (Pascual-Salcedo, D., et al., Rheumatology, 2011, 50, 1445-1452; Plasencia, C., et al., Ann Rheum Dis, 2012, 71, 1955-1960).

As long as the relative amount of the anti-drug antibodies (ADA) is lower than the serum trough level of IFX, the drug can provide a clinical benefit (de Vries, M K., et al., Ann Rheum Dis, 2007, 66, 1252-1254). However, when the endogenous production of antibodies exceeds the amount of drug in the serum, the latter is cleared from the circulation (de Vries, M K., et al., Ann Rheum Dis, 2007, 66, 1252-1254) and the therapy is rendered ineffective.

The accelerated clearance of the biological drug complexed to antibodies may result in decreased pharmacological availability and ultimately in the loss of therapeutic effectiveness of the drug (Jamnitski, A., et al., Ann Rheum Dis, 2011, 70, 284-288). Therefore, it is very likely that the equilibrium between DL (for example, levels of IFX) and the LADA regulates the overall effectiveness of the drug (de Vries, M K., et al., Ann Rheum Dis, 2007, 66, 1252-1254). Moreover, the formation of anti-biological drug antibodies is strongly related to the development of infusion-related reactions (Pascual-Salcedo, D., et al., Rheumatology, 2011, 50, 1445-1452). Patients with high levels of anti-biological drug antibodies have a higher risk of suffering from an infusion-related reaction than patients with low anti-biological drug antibody levels. Infusion-related reactions are defined as hypersensitivity adverse effects occurring during the biological drug infusion or a few hours after the infusion. Infusion-related reactions are type III hypersensitivity reactions, occurring by the deposition of biological drug-anti-biological drug antibody immune complexes in tissues. Such depositions can induce inflammation, and symptoms are tachycardia, erythema, shortness of breath, headache, fever, itching, among others.

Currently, several assays and technologies have been reported for the analysis of trough DL and LADA (Gorovits, B., AAPS J, 2009, 11, 133-138). While most of the methods deliver accurate and sensitive results for measurement of DL, discrepancies or differences are found between the different ADA assays disclosed in the state of the art:

Bridging ELISA is the most commonly used assay for immunogenicity screening in both clinical drug development and in clinical settings (Gorovits, B., AAPS J, 2009, 11, 133-138). Bridging ELISA shows high specificity, adequate sensitivity and is amenable to automation. However, bridging ELISA is a method highly susceptible to drug interference and it is normally not able to detect ADA of low affinity or low avidity due to sample dilution and the multiple washing steps required by the technique (Pan, J. et al., Journal of Pharmacological and Toxicological Methods, 2011, 63, 150-159).

Fluid and solid phase radioimmunoassay (RIA) are sensitive methods to quantify LADA and they are less prone to drug interference (Hart, M H., et al., J Immunol Methods, 2011, 372, 196-203). However, these methods require the use of facilities adapted for the use of radioisotopes. Solid phase RIA for LADA testing uses an approach where serum IgG are bound by agarose-immobilized protein A, and incubated overnight with 125I-labeled IFX, before measuring radioactivity (Jamnitski, A., et al., Ann Rheum Dis, 2011, 70, 284-288). However, to date, there is no human standard available to construct a calibration curve for LADA testing, so most assays provide immune response results (i.e., LADA) as arbitrary units.

Cell-based assays can provide information on the biological relevance of the immune response (i.e. detection of neutralizing antibodies) (Lallemand, C., et al., J Immunol Methods, 2011, 373, 229-239). In addition, it is known that all human antibodies to biological drugs such as IFX and adalimumab are anti-idiotypic and therefore neutralizing by definition (van Schouwenburg, P A., et al., Ann Rheum Dis, 2012, 72, 104-109). The main limitation of cell-based assays is that they may require facilities for cell culturing,—80° C. storage and a luminometer, which may not be readily available in a clinical laboratory.

Other methods including homogeneous mobility shift assays (HMSA) have been recently reported to have a very high drug tolerance and detect ADA in the presence of virtually any concentration of drug. Therefore, said methods are not limited to the testing of trough levels (Wang, S L., et al., J Immunol Methods, 2012, 382, 177-188). However, the applicability of the specific technology underlying these methods in a normal clinical laboratory is questionable.

For LADA determination, the most commonly used ELISA-based assay is the bridging ELISA, which takes advantage of the bivalency of immunoglobulin (IgG) types 1, 2 and 3 to cross-link the ADA with both immobilised and labelled drug molecules (Pascual-Salcedo, D., et al., Rheumatology, 2011, 50, 1445-1452; Plasencia, C., et al., Ann Rheum Dis, 2012, 71, 1955-1960). This is also the assay format implemented in commercially available ELISA assays (Llinares-Tello, F., et al., Rheumatol Int, May 10, 2014; Chen, D Y. et al., Jan. 17, 2014). Bridging ELISA is also one of the assay structures disclosed in Tornetta, M., et. al. (Tornetta, M., et. al., Journal of Immunological Methods, 2007, 328, 34-44). In said document, following structure and steps are described for the ELISA bridging assay: 1. coating of the plate: Ab1 (human antibody directed against human IL-13); 2. incubation with anti-drug antibodies (mAb2, mAb4, two murine hybridoma antibodies specific to Ab1 (C188, C189) or anti-serum from a monkey immunized with Ab1 (poly-35); 3. incubation with biotinylated Ab1; 4. incubation with streptavidin-HRP; and 5. addition of Tetramethylbenzidine. A similar bridging ELISA assay structure is seen in Abd Serotec (Abd Serotec, "Effective Tools for Drug Monitoring Assays", 2008, 1-2).

Said bridging ELISA is also shown as a method with potential for routine adaptation in a hospital clinical setting for patient monitoring for the testing of anti-drug antibodies, by Ruiz-ArgüUello, B., et. al. (Ruiz-ArgüUello, B., et. al., Clin Chem Lab Med, 2013, 51(12), e287-e289).

Testing of DL and LADA is mostly performed using blood samples collected immediately before administration of a new infusion to measure the so-called trough levels, i.e. the measurement performed when the patient has the lowest levels of drug present in the body when said patient is being administered a drug periodically.

Current testing requires a clinical extraction of the serum sample followed by a labor-intensive and time-consuming ELISA and is only performed by specialized laboratories. As a consequence, test results are not immediately available to act upon when administrating the scheduled infusion.

Novel methods under the point-of-care (POC) testing format provide advantages over the previously mentioned techniques, in terms of test simplicity and speed. Although POC devices have been described for applications related to monitoring therapies with biological drugs, there remain several drawbacks. For example, a POC device was previously described as a rapid lateral flow-based assay for on-site monitoring of serum trough levels of IFX (Corstjens, P L., et al., Anal Bioanal Chem, 2013, 405, 7367-7375). The method includes a three-step procedure on strips with immobilized TNF-α as capture molecule: flow of diluted sample, flow of wash buffer and flow of labeling reagent. The label, luminescent up converting phosphor (UCP) particles coating protein-A, emits a 550 nm visible light upon excitation with 980 nm infrared light. IFX concentrations are determined through measurement of UCP fluorescence at the test line. Another example is an immunochromatographic assay developed for the detection of antibodies against rabies virus and with the following configuration or structure: sample pad (where the sample is applied); conjugate pad (with the conjugate colloidal gold-RABV G); test line (with staphyloccal protein A); and control line (with affinity purified anti-RABV G monoclonal antibodies).

It has also been disclosed a lateral flow-based assay for the detection of ADA generated against IFX (Pan, J. et. al., Journal of Pharmacological and Toxicological Methods, 2011, 63, 150-159). The assay comprises a preincubation step of the serum samples with both drug (for example, IFX) covalently linked to biotin and drug (for example, IFX) covalently linked to an organic hapten. Said mixture is then applied to a test strip that contains releasable streptavidin-coated gold particles dried on a pad attached to a membrane comprising a test zone or line with anti-hapten antibodies. Result of the test can be detected by presence or absence of a visible red line formed at the test zone or line. However, as mentioned above, this assay requires a preincubation step that lasts for several hours not allowing, hence, obtaining instant results to take a decision on the next dose to be applied in the treatment.

Hence, there is still the need of a diagnostic tool that allows rapid or almost instant and simple detection of LADA with minimal manipulation of the sample allowing, thus, a more frequent monitoring and a better and personalized administration of the biological drug based on the trough levels of the patient just before next administration.

The present inventors have found a lateral flow immunoassay structure that overcomes all prior art drawbacks. More specifically, the lateral flow immunoassay of the present invention is small, portable, simple, fast, easy to use and cost-effective. In addition, it does not need a qualified operator, additional equipment, or additional manipulation of the sample extracted from the patient and, hence, it dramatically reduces operating times and resources required to ascertain whether an individual has ADA. Therefore, the present invention allows a rapid, almost instantaneous, on-site qualitative detection of ADA in patients that would simplify and accelerate clinical decision in the course of biological therapy in autoimmune and inflammatory disease giving the possibility to take decisions on the next dose of biological drug to administer on the basis of the results of the assay.

Therefore, the present invention refers to a lateral flow immunoassay for the detection of ADA based on an immunochromatographic system.

In even further embodiments, the present invention discloses a device to carry out said lateral flow immunoassay.

In a further embodiment, the present invention refers to a kit to carry out lateral flow immunoassay of the present invention.

In an additional embodiment, the present invention refers to the use of the lateral flow immunoassay according to the present invention for the detection of ADA in a sample of a patient and, hence, predicting a loss or reduction in the effectiveness of the therapy being administered to said patient.

In a further embodiment, the present invention discloses a method of modulating a biological drug treatment administered to a patient in need thereof on the basis of the result of the lateral flow immunoassay mentioned above.

Additionally, the present invention also refers to a method of predicting whether a patient will respond or not to a treatment or a further dose of a treatment on the basis of the result of the lateral flow immunoassay of the present invention.

In another embodiment, the present invention refers to a method of determining whether a patient should receive a further dose of a treatment on the basis of the result of the lateral flow immunoassay of the present invention.

As used herein, the terms "biological sample", "sample" and their plurals are used interchangeably and refer to a sample obtained from a patient or an individual to be tested for the presence of ADA.

As used herein, "drug", "biological drug" and their plurals are used interchangeably and refer to drugs consisting of or comprising biological molecules or material, i.e. both, proteins, polypeptides, peptides, polynucleotides, olygonucleotides, polysaccharides, oligosaccharides and fragments thereof, as well as cells, tissues, biological fluids or extracts thereof, and which induce antibodies in patients.

As used herein, the term "infliximab" refers to the infliximab chimeric monoclonal antibody, which is the active moiety of many brand molecules and biosimilar drugs like, but not limited to, Remicade®, Remsima®, and Inflectra®, and also to fragments of said molecule which induce an immunological response in patients which is similar to that obtained with complete IFX.

As used herein, the term "membrane" and its plural refer to a support surface where the biological drug and, if required, the biological drug conjugated to a detectable label can be applied according to methods known in the state of the art, for example, covalent binding and/or drying, respectively.

As used herein, the term "modulate" and its plural and derivatives refer to increasing, decreasing or maintaining a particular quantity.

As used herein, the terms "patient" and "individual" and their plurals are used interchangeably to refer to subjects to be tested for the presence of ADA.

As used herein, "treatment" and its plural refer to treatments based on or that comprise the use of one or more biological drugs.

As used herein, "trough level" and its plural refer to the lowest concentration level at which a medicine is present in the body. Biological drugs, such as Infliximab, are administered periodically (for example, every eight weeks, approximately), therefore, a trough level of a biological drug, such as Infliximab, is the moment just before the infusion of the next dose. The optimum moment for testing trough levels is the day that the patient goes to the day hospital to receive the treatment, before the infusion, or within the 24 hours previous to the infusion, or within the 48 hours previous to the infusion, or within the 72 hours previous to the infusion.

Therefore, as stated above, in one aspect the present invention refers to a lateral flow immunoassay for the detection of ADA against a biological drug, based on an immunochromatography system, comprising: a membrane comprising:
- a capture area;
- a sample application area;
- a flow path from the sample application area to the capture area; and
- a conjugate area located in the flow path, characterized in that the conjugate area comprises said biological drug detectably labeled and the capture area comprises said biological drug immobilized thereto.

In a preferred embodiment, the biological drug is a monoclonal antibody, chimeric, human, humanized, human Fab fragments or fusion molecule used in therapy against inflammatory and/or autoimmune disease. In the most preferred embodiment, the biological drug is IFX. Hence, in the preferred embodiment the present invention refers to a lateral flow immunoassay for the detection of ADA against IFX comprising IFX detectably labeled in the conjugate area and IFX immobilized in the capture area.

The membrane used in the lateral flow immunoassay of the present invention can be made of a variety of materials which the sample to be tested can pass or move through and that are known for a person skilled in the art. For example, the materials used to form the membrane can include, but are not limited to, natural, synthetic, or naturally occurring materials that are synthetically modified, such as polysaccharides (for example, cellulose materials such as paper and cellulose derivatives as cellulose acetate and nitrocellulose); polyether sulfone; nylon; silica; inorganic materials, such as deactivated alumina, diatomaceous earth, $MgSO_4$, or other inorganic finely divided material uniformly dispersed in a porous polymer matrix such as vinyl chloride, vinyl chloride-propylene copolymer, and vinyl chloride-vinyl acetate copolymer; cloth, both naturally occurring (for example, cotton) and synthetic (for example, rayon); porous gels, such as silica gel, agarose, dextran, and gelatin; polymeric films, such as polyacrylamide; and the like. In a preferred embodiment, the membrane is a nitrocellulose membrane. There are different types of nitrocellulose membranes commercially available according to their absorbent capacity and capillary flow, for example, MDI® 15µ SS12, Sartorius® CN140, Millipore® HF180, Sartorius® CN150, MDI® 5µ SN12, MDI® 8µ SN12, MDI® 10µ SN12, MDI® 150-SS40, MDI® 200-CNPH-SS60, Whatman® FF170, Whatman® FF120 or the like. In the most preferred embodiment, the nitrocellulose membrane is MDI® 8µ SN12.

In a preferred embodiment the capture area comprises one or more test lines comprising the biological drug immobilized thereto. In the most preferred embodiment the capture area comprises one test line.

Said drug can be immobilized to the membrane by means known by the person skilled in the art. In a particular embodiment, the biological drug (for example, IFX) is immobilized in the membrane at a concentration of between 1 mg/ml to 3 mg/ml, preferably of 1 mg/ml, by using an appropriate immobilization buffer, for example, borate buffer saline (BBS), sucrose, carbonate buffer pH 10.5 plus sucrose and 150 mM NaCl, borate buffered saline plus 1 mg/ml Rabbit IgG, carbonate buffer pH 10.5 plus sucrose, BBS plus 3% sucrose, BBS plus 1% Bovine Serum Albumin, BBS plus 3% Trehalose, BBS plus 1% casein (alkalized), BBS plus 1% casein, or the like, preferably BBS. IFX is diluted into said appropriate immobilization buffer and cards laminated with strips of nitrocellulose are striped to produce the test line with the IFX solution mentioned above at a rate calculated to give optimal performance using a bench-top iso-flow machine. Once coated, nitrocellulose strips are immediately placed into a drying oven at 37° C. for incubation overnight (for example, for 16-24 hours) to ensure IFX is properly immobilised to the nitrocellulose.

It is also contemplated that the capture area comprises one or more control lines comprising control molecules immobilized thereto, to confirm that the lateral flow immunoassay of the present invention has worked correctly and, hence, the results provided by the one or more test lines are credible and correct. Immobilization of said control molecules is performed as explained above. In a preferred embodiment the capture area comprises one control line that comprises anti-chicken IgY antibodies immobilized thereto by any of the means mentioned above.

In a preferred embodiment, the conjugate area is formed of or comprises a conjugate pad that comprises the biological drug detectably labeled. It is contemplated that said pad is made of a bibulous, porous or fibrous material capable of absorbing liquid rapidly. The porosity of the material can be unidirectional (for example, with pores or fibres running wholly or predominantly parallel to an axis of the structure) or multidirectional (for example, omnidirectional, so that the member has an amorphous sponge-like structure). Porous plastics material, such as polypropylene, polyethylene, polyvinylidene flouride, polyester, ethylene vinylacetate, acrylonitrile and polytetrafluoroethylene can be used. It can be advantageous to pre-treat the material with a surface-active agent during manufacture, as this can reduce any inherent hydrophobicity in the material and, therefore, enhance its ability to take up and deliver a moist sample rapidly and efficiently. Porous structure can also be made from paper or other cellulosic materials, such as nitrocellulose. Preferably, the material chosen is such that the porous material can be saturated with aqueous liquid within a matter of seconds. Also, preferably, the material remains robust when moistened. In a preferred embodiment, the conjugate pad is made of polyester.

In an embodiment, said conjugate pad is positioned in fluid communication with the membrane and, more preferably, said conjugate pad is mounted on the membrane overlying partially or totally the membrane.

It is contemplated that the detectably labeled biological drug is deposited in the membrane. In one embodiment, said detectably labeled biological drug is deposited in the pad superficially forming, thus, a superficial layer. In another embodiment, the detectably labeled biological drug applied in the pad, can penetrate until the membrane and, in some cases it may also penetrate said membrane.

In a further embodiment, the detectably labeled biological drug is directly applied in the membrane.

In an additional embodiment, the detectably labeled drug is placed in the membrane or in the conjugate pad by means of techniques and procedures known by the person skilled in the art. In the most preferred embodiment, said detectably labeled biological drug is sprayed or spotted over the membrane in the conjugate area or on the pad positioned in the conjugate area, more preferably sprayed. Then, the detectably labeled drug applied is dried. Said drying is preferably performed at 37° C. during 20 minutes.

Moreover, the biological drug located in the conjugate area can be labeled with any moiety or reagent that allows direct detection, i.e. without needing to apply further reagents, reducing, thus, manipulation of the sample and the number of interactions or reactions required to obtain a detectable signal.

Said detectable label can be covalently or non-covalently bound/coupled to the biological drug. The binding/coupling can be accomplished by any method known in the art.

In a preferred embodiment, the detectable label is a metal colloidal particle, more preferably a gold colloidal particle, for example, gold microparticles or gold nanoparticles. In the most preferred embodiment the gold colloidal particles used as a detectable label have a diameter of between 20 nm and 80 nm, even more preferably, of between 20 nm and 40 nm. In the most preferred embodiment, gold colloidal particles of 40 nm diameter are used to label the biological drug (for example, IFX) and gold colloidal particles of 20 nm diameter are used to label the control molecule (for example, chicken IgY).

In a preferred embodiment, when gold colloidal particles are used as detectable label, the concentration of the biological drug conjugated to said particles deposited in the conjugate area or the conjugate pad is 10 Gold Units to 120 Gold Units, more preferably 70 Gold Units, according to international units. In another preferred embodiment, the concentration of the biological drug (for example, IFX) conjugated to said gold colloidal particles deposited in the conjugate area is 40 Gold Units and the concentration of the control molecule (for example, IgY) conjugated to said gold colloidal particles deposited in the conjugate area is 15 Gold Units, both according to international units.

Briefly, Gold Units are measured by diluting concentrated biological drug conjugate with conjugate re-suspension buffer (for example, sodium phosphate buffer) and measuring Optical Density (OD) at a specific wavelength of 520 nm using a spectrophotometer, previously blanked against conjugate re-suspension buffer. Biological drug conjugate OD is then used as a measure of the total amount of gold added to each test. For example, 1 µl of OD 20 units conjugate is equal to 20 Gold Units. Therefore, for a requirement of 70 Gold Units per test, 3.5 µl of liquid conjugate will be required per test-strip from a calculated OD of 20 units of concentrate biological drug conjugate.

Detection of the detectable label will depend on the chosen moiety or reagent, and can be done by any of the methods known in the state of the art, for example, visual inspection, ultraviolet and visible spectrophotometry, fluorimetry, radioactivity counting or the like. In a preferred embodiment, when gold particles are used as detectable labels, the results of the assay are obtained and analyzed by visual inspection.

In a further embodiment, the conjugate area also comprises detectably labeled control molecules that will flow with the sample without reacting with the content of the same and will bind to the one or more control lines to confirm whether the lateral flow immunoassay of the present invention has worked correctly and, hence, the results provided by the one or more test lines are credible and correct. The molecule used depends on the one immobilized in the at least one control line of the capture area. In addition labels used for the control molecules and labeling are as explained above.

In a preferred embodiment, as mentioned above, the capture area comprises one control line that comprises anti-chicken IgY antibodies immobilized thereto and, hence, the conjugate area comprises detectably labeled immunoglobulin Y (IgY) from chicken.

In one embodiment, the label used for the control molecules can be the same as that used for the one or more biological drugs tested as long as it is possible to distinguish the results obtained for each drug by other means, for example, through the position of the test line. In another embodiment, the label used for the control molecules is different from that used for the one or more biological drugs tested, giving distinguishable signal.

In a preferred embodiment, the sample application area is formed by or comprises a sample pad which is located before the conjugate area and is in fluid communication with said conjugate area, more preferably, said sample pad is overlying partially or totally the conjugate area or is overlaid partially or totally by the conjugate area. In a further embodiment the sample pad is mounted on the membrane or on the conjugate pad.

Furthermore, it is contemplated that the sample application area is adapted to the biological sample which is intended to be analyzed. For example, in case whole blood is the biological sample to be analyzed, the sample application area may comprise a blood separation pad for receiving the sample, wherein the blood separation system is then fluidly coupled to the conjugate structure. In one embodiment, the blood separation pad partially or totally overlays the conjugate pad.

In a preferred embodiment, the whole blood sample is applied to the blood separation pad made, for example, of absorptive material/pad that is fluidly coupled to the conjugate area. For example, the blood separation pad can function as a filter, for example, to remove red blood cells and other cellular and solid components such as fibrin and clots are retained from the sample. Filtered sample can then reach the conjugate area. The blood separation pad can also function as an adsorbent that removes interfering factors from the sample by adsorption. There are several blood separation pads commercially available, for example, MDI® FR-1 (0.6) pad, MDI® FR-1 (0.35) pad, Whatman® MF-1 pad, Ahlstrom® Cytosep 1660 pad, Ahlstrom® Cytosep 1662 pad, paper pad treated with PHA, or the like. In the most preferred embodiment, the blood separation pad used is MDI® FR-1 (0.6) pad.

In a further preferred embodiment, a distal absorbent pad fluidly coupled to the membrane is provided. Said distal absorbent pad is configured to absorb the liquid or fluid coming from the membrane and, hence, cause the sample to move from the sample application area to said distal absorbent pad circulating through the whole lateral flow immunoassay structure, i.e. going through the conjugate area and the capture area. Therefore, this distal absorbent pad can be made of any absorbent material, for example, Whatmann® paper, filter paper or chromatography paper. In a preferred embodiment, the absorbent material is a filter paper, more preferably the filter paper is a paper pad from Ahlstrom® (product code 222), which has an advantageous behavior or performance because it is relatively thin and has a highly absorbent nature as it is made from compressed paper.

In an additional embodiment, the lateral flow immunoassay of the present invention can detect ADA against two or more biological drugs. In this case, the capture area would comprise at least one test line for each of the biological drugs analyzed with the corresponding biological drug immobilized thereto. In addition, the conjugate area would be provided with each of the biological drugs detectably labeled. The label used for each of the biological drugs tested and labeling can be as mentioned above. Moreover, it is contemplated that the labels used for the different biological drugs tested are the same as long as it is possible to distinguish the results obtained for each drug tested by other means, for example, through the position of the test line. In another embodiment, the labels used for each of the biological drugs are different, giving each of them a distinguishable signal.

In a preferred embodiment, the lateral flow immunoassay of the present invention allows the detection of ADA of any isotype present in a patient, i.e. IgG, IgA, IgE, IgM and IgD. More preferably, the lateral flow immunoassay of the present invention allows the detection of ADA of the isotype IgG and, even more preferably IgG of types 1, 2 and/or 3, that is the main isotype that characterizes the immune response to a biological drug.

In a further embodiment, the lateral flow immunoassay based on an immunochromatography assay described above, is in the form of an immunocromatography test strip.

In a particular embodiment, for the lateral flow immunoassays and immunocromatography test strips of the present invention the biological sample, preferably whole blood, is directly applied to the sample application area. For example, a whole blood drop (from 20 µl to 40 µl, preferably 30 µl) obtained from a finger prick (for example, using a needle), without any type of previous dilution or previous treatment of the sample with reagents or solutions, is enough for use and analysis with the lateral flow immunoassays and immunocromatography test strips described above. No additional serum or plasma extraction is required.

Then, a simple chase buffer, more preferably, standard PBS buffer, is applied to the sample application area to allow the whole blood sample to flow by capillarity along the assay or strip through the flow path to react with the chemical reagents and components used in the lateral flow immunoassay. Preferably, 100 µl of chase buffer are added. Said chase buffer can be added by any means available to a person skilled in the art, for example a lab pipette adjusted to 100 µl or a simpler plastic pipette. The chase buffer can be added 60 seconds after sample application, more preferably 50 seconds after sample application, even more preferably 40 seconds after sample application, and most preferably 30 seconds after sample application.

When serum or plasma are used for analysis with any of the lateral flow immunoassays of the present invention, between 10 µl and 20 µl, preferably 15 µl of sample can be added to the sample application area and the same procedure described above is performed.

For any other biological sample to be used with the lateral flow immunoassays of the present invention, for example interstitial fluid, saliva, ocular fluid, cerebral spinal fluid, sweat, urine, milk, ascites fluid, synovial fluid, peritoneal fluid, semen, vaginal fluid, amniotic fluid or the like, is within the skills of the person skilled in the art to determine the quantity of sample required to correctly perform the assays described above.

First, as mentioned above, the biological sample is applied to the sample application area and the fluid will contact the sample pad, if present. The sample pad (for example, a blood sample pad) acts as a filter for solid components, thereby allowing the flow-through of the liquid component. The conjugate area, more preferably in the form of a conjugate pad where the conjugated biological drug, preferably IFX, is deposited, is located after the sample application area (it can be located partially overlapped to the sample pad), both pads being mounted on the membrane strip, preferably made of nitrocellulose. The biologic drug conjugated to a detectable label, preferably gold colloidal particles will recognize, react and bind the ADAs against said biological drug in the biological sample, if present. Hence, biological drug-ADA immunocomplexes will be formed that will be conjugated with gold colloidal particles.

As mentioned previously, optionally, a control molecule, also conjugated with a detectable label, preferably gold colloidal particles, can be deposited on the conjugate pad too. In a preferred embodiment, such a control molecule is immunoglobulin Y (IgY) from chicken. If present, this control molecule, at this stage, will not specifically recognize, react and bind components present in the biological sample.

The fluid sample containing the drug-ADA immunocomplexes conjugated to gold colloidal particles and, optionally, the control molecule conjugated to gold colloidal particles, will flow through the flow path from the conjugate pad to the nitrocellulose strip where capture elements are immobilized in at least one test line and, optionally, also in at least a control line.

The at least one test line comprises a specific capture reagent that, as mentioned above is the same biologic drug molecule present in the conjugate pad, preferably IFX, immobilized on the membrane strip. The bivalent nature of the ADA molecules present in the sample, preferably IgG, allows the reaction of the drug-ADA immunocomplexes conjugated to gold colloidal particles with the immobilized biologic drug that will bind said immunocomplexes through the available epitope in the ADA molecules, if present in the biological sample. The test or assay is allowed to develop for 5 to 60 minutes, more preferably 30 minutes.

Therefore, when the reactions described above take place, a red band will be visually distinguishable in the at least one test line of the lateral flow immunoassay of the present invention as a result of specific bridge binding between ADA and the biological drug present in the conjugate area and in the capture area. This positive result will be indicative of the presence of ADA in the biological sample tested.

The at least one optional control line comprises a specific capture reagent that is a molecule, immobilized on the membrane strip, which reacts with the control molecule. In a preferred embodiment, such a reagent is anti-chicken IgY antibody. A reaction will take place between the immobilized anti-chicken IgY antibody and the chicken IgY antibody that migrates with the sample fluid. A red band will be visually distinguishable in the control line of the device as a result of this binding between control molecules and will validate the result in the test line. Said results are measured by visual scoring, preferably by Rann score; and/or by reader or scanner that uses a densitometric method for analysis, preferably by Camag analysis.

The rationale, fundamentals and interpretation of the detection techniques mentioned above are known by the person skilled in the art. Briefly, Rann Score determines line intensity in a quantification scale ranging from 0 to 10 Units by comparison with a well-defined reference card; and Camag analysis determines line intensity by scanning the strips from top to bottom and performing thereby a densitometric analysis in a scale from 0 to 1000 Units.

In case the biological sample, preferably a whole blood sample, does not contain the ADA against the biological drug, no red band will appear at the at least one test line as a result of no formation of drug-ADA immunocomplexes in the conjugate pad and no subsequent reaction with the biological drug immobilized on the membrane strip in the capture area. If the at least one optional control line exists in the device, a red band will be visually distinguishable at the least one control line as a result of the reaction between IgY from chicken conjugated with gold colloidal particles control molecules and anti-chicken IgY antibodies immobilized on the membrane strip in the capture area.

If the at least one control line is present and gives no signal, the result of the lateral flow immunoassay of the present invention will not be valid.

In another embodiment, the present invention refers to a device to carry out the lateral flow immunoassay of the present invention that comprises:

a lateral flow immunoassay membrane as described above; and a container.

The container can be made of any material know in the art that allows the protection of the membrane used to carry out the lateral flow immunoassay of the present invention. Preferably, the container is made of plastic.

In addition, it is noted that the container has an structure that allows the application of the sample and the visualization of the results of the test without removing said container.

In a preferred embodiment, the device of the present invention is a single use device.

In an additional embodiment, the device of the present invention further comprises a lancet and a blood collection component.

In another embodiment, the present invention refers to a kit to carry out the lateral flow immunoassay of the present invention comprising:

a device as described above; and instructions to carry out the assay.

In a further embodiment, the present invention refers to the use of the lateral flow immunoassays of the present invention and, hence, of devices and kits comprising said lateral flow immunoassays or allowing to carry them out, to detect ADA against a biological drug in a biological sample from a patient. The presence of ADA in the biological sample from a patient would indicate or predict that a loss or reduction of the effectiveness of the drug is to be expected if said drug is further administered to the patient.

The biological sample used can be whole blood, plasma, serum, interstitial fluid, saliva, ocular fluid, cerebral spinal fluid, sweat, urine, milk, ascites fluid, synovial fluid, peritoneal fluid, semen, vaginal fluid, amniotic fluid or the like. In a preferred embodiment, the biological sample used is whole blood, plasma or serum, more preferably whole blood.

As stated above, in the most preferred embodiment of the present invention, the use of the lateral flow immunoassay allows the detection of the presence or absence of ADA against IFX in a biological sample from a patient. The presence of ADA against IFX in said biological sample from the patient indicates or predicts that a loss or reduction of the effectiveness of IFX is to be expected if IFX is further administered to the patient.

In a further preferred embodiment, the above-mentioned use of the lateral flow immunoassays of the present invention is performed to measure trough levels of ADA in the patient. For this reason, measurement of levels is performed within 72 hours before the infusion of the next dose of the biological drug, preferably within 48 hours before the infusion of the next dose of the biological drug, more preferably within 24 hours before the infusion of the next dose of the biological drug and even more preferably just before the infusion of the next dose of the biological drug. Hence, in the most preferred embodiment trough levels of ADA against the biological drug are measured.

In an additional embodiment, the present invention refers to a method of modulating a biological drug treatment administered to a patient in need thereof, comprising the steps of:

a) a first step of obtaining a biological sample from the patient;

b) a second step of analyzing the biological sample using a lateral flow immunoassay of the present invention as described above configured to detect ADA against said biological drug; and c) a third step of modulating the next biological drug dose to be administered to the patient on the basis of the results obtained in step b).

The biological sample used can be whole blood, plasma, serum, interstitial fluid, saliva, ocular fluid, cerebral spinal fluid, sweat, urine, milk, ascites fluid, synovial fluid, peritoneal fluid, semen, vaginal fluid, amniotic fluid or the like. In a preferred embodiment, the biological sample used is whole blood, plasma or serum, more preferably whole blood.

In a preferred embodiment, step c) comprises maintaining the dose of biological drug in case the result of the lateral flow immunoassay performed in step b) is negative.

In a further preferred embodiment, step c) comprises increasing the dose of biological drug in case the result of the lateral flow immunoassay performed in step b) is positive.

In an additional preferred embodiment, step c) comprises stopping the administration of biological drug in case the result of the lateral flow immunoassay performed in step b) is positive.

It is contemplated that the biological sample of the first step is obtained within 72 hours before the infusion of the next dose of the biological drug, preferably within 48 hours before the infusion of the next dose of the biological drug, more preferably within 24 hours before the infusion of the next dose of the biological drug and even more preferably just before the infusion of the next dose of the biological drug. In the most preferred embodiment, in step b) the method measures trough levels of ADA against the biological drug in the patient.

In a further preferred embodiment the patient has an autoimmune and/or inflammatory disease and is being treated with a biological drug, more preferably, the patient has psoriasis, Crohn's disease, ankylosing spondylitis, psoriatic arthritis, rheumatoid arthritis or ulcerative colitis and is being treated with a biological drug.

In the most preferred embodiment, the biological drug is IFX.

Additionally, in a further embodiment, the present invention also refers to a method of predicting whether a patient will respond or not to a treatment with a biological drug or a further dose of a treatment with a biological drug comprising the steps of:

a) a first step of obtaining a biological sample from the patient;

b) a second step of analyzing the biological sample using a lateral flow immunoassay of the present invention as described above configured to detect ADA against said biological drug; and c) a third step of determining whether a patient will respond or not to a treatment with a biological drug or a further dose of a treatment with a biological drug on the basis of the results obtained in step b).

The biological sample used can be whole blood, plasma, serum, interstitial fluid, saliva, ocular fluid, cerebral spinal fluid, sweat, urine, milk, ascites fluid, synovial fluid, peritoneal fluid, semen, vaginal fluid, amniotic fluid or the like. In a preferred embodiment, the biological sample used is whole blood, plasma or serum, more preferably whole blood.

A negative result of the lateral flow immunoassay performed in step b) would mean that the patient is susceptible of responding to a treatment with the biological drug or to a further dose of said biological drug.

A positive result of the lateral flow immunoassay performed in step b) would mean that the patient is susceptible of not responding to a treatment with the biological drug or to a further dose of said biological drug.

It is contemplated that the biological sample of the first step is obtained within 72 hours before the infusion of the next dose of the biological drug, preferably within 48 hours before the infusion of the next dose of the biological drug, more preferably within 24 hours before the infusion of the next dose of the biological drug and even more preferably just before the infusion of the next dose of the biological drug. In the most preferred embodiment, in step b) the method measures trough levels of ADA against the biological drug in the patient.

In a further preferred embodiment the patient has an autoimmune and/or inflammatory disease and is being treated with a biological drug, more preferably, the patient has psoriasis, Crohn's disease, ankylosing spondylitis, psoriatic arthritis, rheumatoid arthritis or ulcerative colitis and is being treated with a biological drug.

In the most preferred embodiment, the biological drug is IFX.

In another embodiment, the present invention refers to a method of determining whether a patient should receive a further dose of a biological drug comprising the steps of:
 a) a first step of obtaining a biological sample from the patient;
 b) a second step of analyzing the biological sample using a lateral flow immunoassay of the present invention as described above configured to detect ADA against said biological drug; and
 c) a third step of determining whether the patient receives a further dose of the biological drug on the basis of the results obtained in step b).

The biological sample used can be whole blood, plasma, serum, interstitial fluid, saliva, ocular fluid, cerebral spinal fluid, sweat, urine, milk, ascites fluid, synovial fluid, peritoneal fluid, semen, vaginal fluid, amniotic fluid or the like. In a preferred embodiment, the biological sample used is whole blood, plasma or serum, more preferably whole blood.

A negative result of the lateral flow immunoassay performed in step b) would mean that a further dose of said biological drug is to be administered to the patient.

A positive result of the lateral flow immunoassay performed in step b) would mean that a further dose of said biological drug should not be administered to the patient.

It is contemplated that the biological sample of the first step is obtained within 72 hours before the infusion of the next dose of the biological drug, preferably within 48 hours before the infusion of the next dose of the biological drug, more preferably within 24 hours before the infusion of the next dose of the biological drug and even more preferably just before the infusion of the next dose of the biological drug. In the most preferred embodiment, in step b) the method measures trough levels of ADA against the biological drug in the patient.

In a further preferred embodiment the patient has an autoimmune and/or inflammatory disease and is being treated with a biological drug, more preferably, the patient has psoriasis, Crohn's disease, ankylosing spondylitis, psoriatic arthritis, rheumatoid arthritis or ulcerative colitis and is being treated with a biological drug.

In the most preferred embodiment, the biological drug is IFX.

Hence, the lateral flow immunoassays and immunochromatography assays described above have a bridge binding format, wherein the ADA, if present in the sample of the patient, acts a bridge binding both the detectably labeled biological drug in the conjugate area and the biological drug immobilized in the capture area. Moreover, surprisingly, this type of structure is obtained without the need of pretreatments or incubations of the sample, only by applying the sample in a membrane or test strip with the structure described herein. In addition, said bridge structure, surprisingly, can be effectively formed within a short time lapse, i.e. from 5 to 60 minutes, a shorter time frame than that described in the prior art.

Therefore, the main advantage of the assays of the present invention is that the proposed assay structure needs no specific manipulation or reaction of the sample obtained with reagents before applying it to the strip. Hence, it allows obtaining results in a very short time frame (5 to 60 minutes). This features, allows the use of the assays described herein to make decisions on the next dose to administer of a biological drug to a patient on the basis of the results obtained in the assay.

In addition, the assay or test configuration provides a small, portable, simple, fast, easy to use and cost-effective device that does not need for qualified operator, nor additional equipment to obtain qualitative information on whether a patient has ADA that can be used to take clinical decisions.

EXAMPLES

Example 1. Lateral Flow Immunoassay Device for the Detection of ADA Against IFX

In this case, the assay used intended to detect ADA against IFX. Hence, the biological drug applied in the conjugate pad and immobilized in the capture area was infliximab. The infliximab drug was obtained as lyophilized powder for perfusion concentrate, reconstituted in water at a concentration of 10 mg/ml and 0.05% sodium azide and immobilized on the nitrocellulose strips. To perform said immobilization, IFX was diluted into BBS immobilization buffer at a concentration of 1 mg/ml and cards laminated with strips of nitrocellulose MDI® 8µ SN12 were striped to produce test line with the IFX solution mentioned above using a bench-top iso-flow machine (1 µl per strip).

A control line to detect the chicken IgY conjugates was generated in the capture area by immobilization of a solution of 0.5 mg/ml of anti-chicken IgY antibodies using a bench-top iso-flow machine (1 µl per strip).

Once coated, nitrocellulose was immediately placed into a drying oven at 37° C. for incubation overnight (for 16-24 hours) to ensure IFX immobilization to the nitrocellulose.

The same stock of the infliximab drug in solution was used for conjugation with 40 nm diameter gold colloidal particles. In addition, chicken IgY were conjugated to 20 nm diameter gold colloidal particles.

After said conjugation, both IFX and chicken IgY conjugates were applied to the polyester conjugate pad mounted on the nitrocellulose strip by spraying with a bench-top iso-flow with an atomising head under pressure, at a calculated spray rate to give 40 Gold Units of IFX and 15 Gold Units of chicken IgY per test strip. The sprayed strips were then dried for 20 minutes at 37° C.

In the lateral flow immunoassay tested, the blood separation pad was the MDI® FR-1 0.6 blood separation pad (MDI®, India). Moreover, a distal absorbent pad of paper pad from Ahlstrom® (product code 222) (Ahlstrom®, Finland) was positioned distally to the membrane to help the sample to flow through the membrane.

Figure 3:
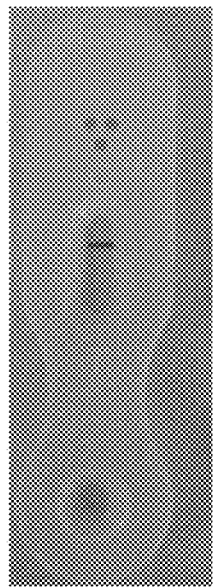
FIG. 3 shows the results of a lateral flow immunoassay of the present invention for a negative serum sample obtained from a healthy individual (A) and a positive serum sample obtained from a patient treated with infliximab and containing 753 U/ml of ADA against IFX (B).
Figure 3:
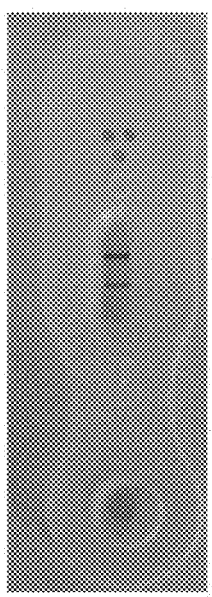

Firstly a human serum sample from a healthy individual and a positive serum sample obtained from a patient treated with IFX containing 753 U/ml (determined with Promonitor® anti-IFX ELISA kit) (1 unit/ml corresponds to 10 ng/ml of IgG antibodies) of ADA against IFX were tested. In both cases 20 µl of serum samples were used. After 30 seconds from the application of the sample, 100 µl of chase PBS buffer (0.01 M Phosphate Buffer, 0.0027 M Potassium Chloride and 0.137 M Sodium Chloride, pH 7.4) were applied. The sample moved across the sample application area, the conjugate pad and through the nitrocellulose strip until the capture area. The assay or test was allowed to develop or react during 30 minutes and afterwards it was visually analyzed. FIG. 3 shows the results obtained. In FIG. 3A it can be seen that the serum derived from a healthy only produced a visual signal in the control line (red line in the top portion of the strip). On the contrary, in FIG. 3B it can be seen that the positive serum mentioned above produced visual signal in both, the control and the test line, i.e. two red lines, one in the top portion of the strip an another in the lower portion (control and test lines respectively), showing the presence of ADA against IFX.

Blood samples were also tested with the above-mentioned test or assay. A positive whole blood sample was generated by spiking negative whole blood with serum containing 241 U/ml of ADA against IFX (determined with Promonitor® anti-IFX ELISA kit) (1 unit/ml corresponds to 10 ng/ml of IgG antibodies). For said spiking, a volume of 500 µl of a negative whole blood was spinned down (1500 rpm; 10 minutes) and the supernatant (160 µl) was replaced by the same volume of the above-mentioned serum containing 241 U/ml ADA against IFX. 40 µl of the negative whole blood sample and the positive spiked blood sample were used.

Figure 4:
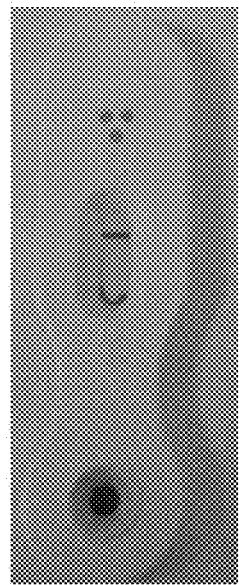
FIG. 4 shows the results of a lateral flow immunoassay of the present invention for a negative (A) and a positive whole blood sample spiked with serum containing 241 U/ml of ADA against IFX (B).
Figure 4:
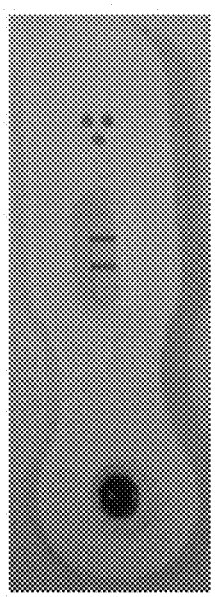

After 30 seconds from the application of the sample, 100 µl of chase PBS buffer (composition mentioned above) were applied. The sample moved across the sample application area, the conjugate pad and through the nitrocellulose strip until the capture area. The assay or test was allowed to develop or react during 30 minutes and afterwards it was visually analyzed. FIG. 4 shows the results obtained. In FIG. 4A it can be seen that the whole blood negative sample produced a visual signal in the control line (red line in the top portion of the strip). On the contrary, in FIG. 4B it can be seen that the positive sample mentioned above produced visual signal in both, the control and the test line, i.e. two red lines, one in the top portion of the strip an another in the lower portion (control and test lines respectively), showing the presence of ADA against IFX.

Example 2. Sensitivity of the Lateral Flow Device in Serum Samples

Figure 5:
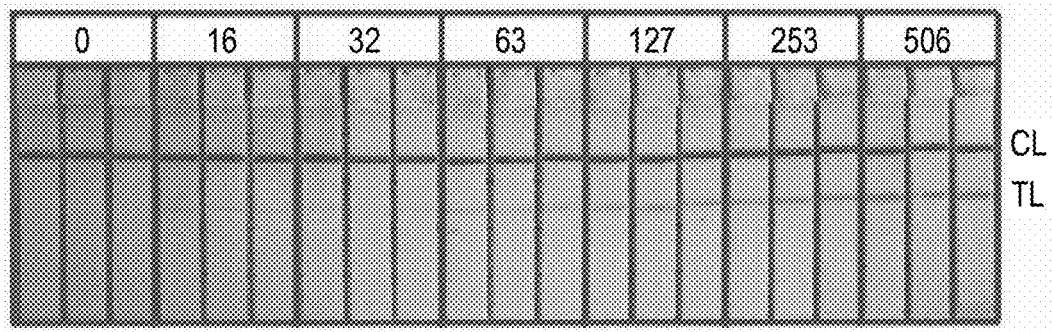
FIG. 5 shows results of a lateral flow immunoassay of the present invention with a dilution series 1:1 from a positive serum sample containing 506 U/ml of ADA against IFX, prepared by serial dilution in a negative serum (A) (CL refers to control line; and TL refers to test line). Said results are analyzed by visual interpretation by Rann score (B) and by reading with an scanner (Camag score) (C).
Figure 5:
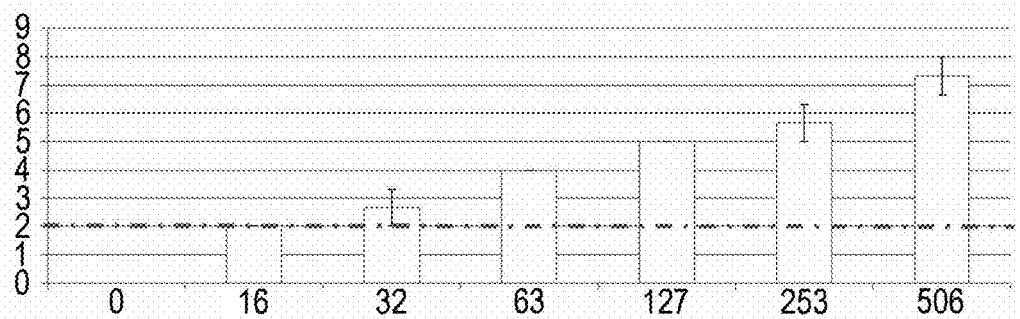
Figure 5:
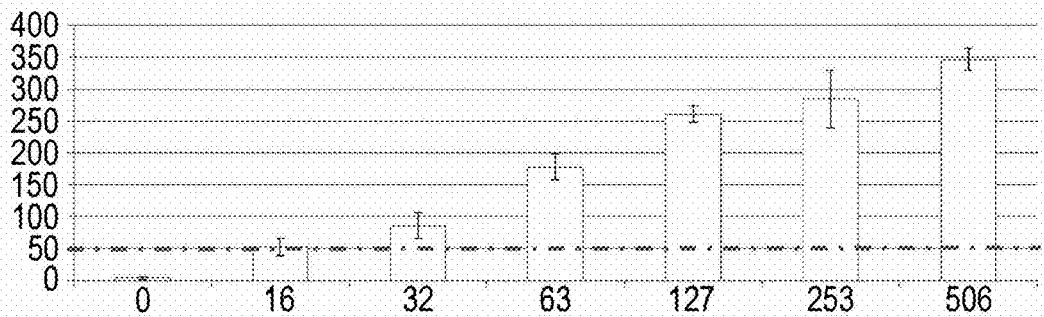

The sensitivity of a lateral flow immunoassay as explained in Example 1 was determined by testing a positive serum sample for anti-infliximab antibodies in serial dilutions (see FIG. 5). A serum sample containing 506 U/ml of ADA against IFX (determined with Promonitor® anti-IFX ELISA kit) (1 unit/ml corresponds to 10 ng/ml of IgG antibodies) was serially diluted 1:1 in another negative serum sample to obtain decreasing levels of ADA from 506 U/ml to 16 U/ml. The negative serum sample was also analyzed as negative control of the experiment. After sample preparation, 20 µl of each serum sample were added to the sample application area of each device using a micropipette. After 30 seconds, 100 µl of chase PBS buffer (same composition as mentioned above) were added to each device and they were left on the bench at room temperature for 30 minutes. Samples were tested in triplicate.

Results were analyzed following two different interpretation methods. First, a visual analysis of the strips was performed by scoring line intensities in a scale from 0 to 10 units using a comparison card (Rann Score). Second, the strips were read using a specific scanner and line intensities were quantified in a numerical scale from 0 to 1000 units (Camag analysis). Results appear summarized in FIG. 5. The analysis of said results revealed decreasing signal intensity in the test line (lower portion of the test strip) throughout the dilution series prepared, in both visual Rann score and Camag score. If a threshold value for positivity was defined at 2 units in the Rann score and at 50 units in the Camag score, 32 U/ml of anti-infliximab antibodies are well detected above those threshold values (FIGS. 5B, 5C). In this experiment, the limit of detection of the lateral flow immunoassay was between 16 U/ml and 32 U/ml for visual analysis, and 16 U/ml if the lateral flow immunoassay was read using a scanner.

Example 3. Sensitivity of the Lateral Flow Device in Blood Samples

The sensitivity of a lateral flow immunoassay as explained in Example 1 in blood samples was determined by testing a blood sample spiked with a positive serum containing 384 U/ml of ADA against IFX (determined using Promonitor® anti-IFX ELISA kit) (1 unit/ml corresponds to 10 ng/ml of IgG antibodies) (see FIG. 6), and serially diluted 1:1 in negative blood sample to obtain decreasing levels of ADA from 384 U/ml to 12 U/ml. The negative blood sample was also analyzed as negative control of the experiment. Same serial dilution was performed with said positive serum and a negative serum. After sample preparation, 15 µl of each serum and 30 µl of each blood sample were added to the sample application area of each device using a micropipette. After 30 seconds, 100 µl of chase PBS buffer (same composition as mentioned above) were added to each device and they were left on the bench at room temperature for 30 minutes. Spiked blood samples and negative blood samples were tested in triplicate while spiked serum samples and negative serum samples were tested in five replicates.

Figure 6:
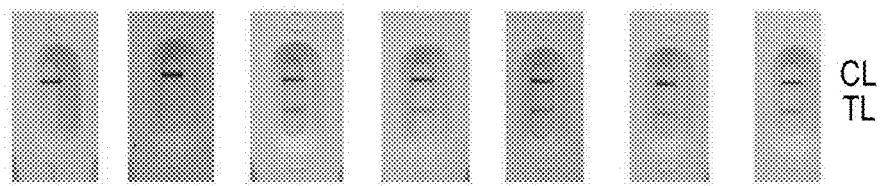
FIG. 6 shows results of a lateral flow immunoassay of the present invention with a positive blood sample for anti-infliximab antibodies, prepared by spiking whole blood with a positive serum containing 384 U/ml of ADA against IFX and preparing further serial dilutions 1:1 of the spiked blood sample with negative blood against IFX, prepared by serial dilution in a negative serum (A) (CL refers to control line; and TL refers to test line). Said results are analyzed by visual interpretation by Rann score (B) and by reading with an scanner (Camag score) (C).
Figure 6:
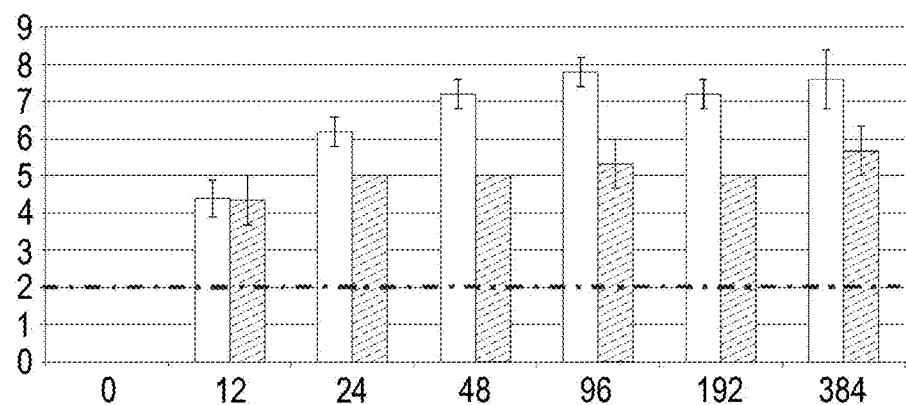
Figure 6:
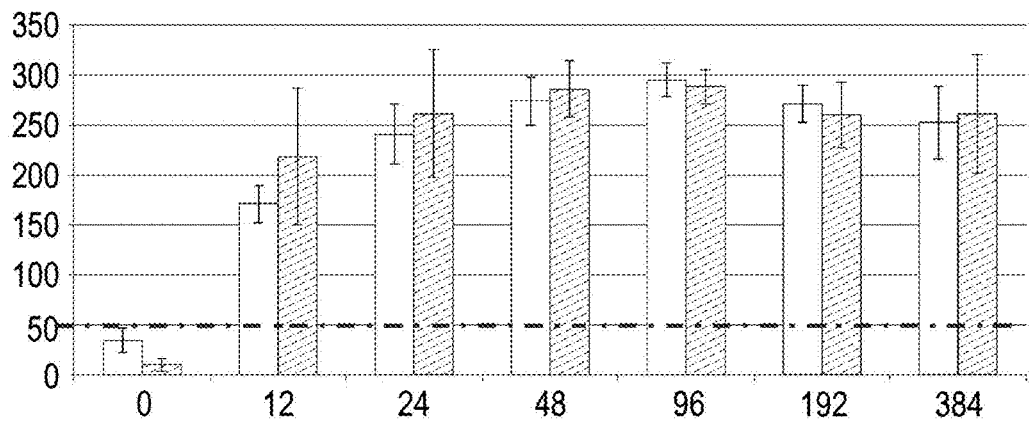

Results were analyzed following two different interpretation methods. First, a visual analysis of the strips was performed by scoring line intensities in a scale from 0 to 10 units using a comparison card (Rann Score). Second, the strips were read using a specific scanner and line intensities were quantified in a numerical scale from 0 to 1000 units (Camag analysis). Results appear summarized in FIG. 6. The analysis of the results showed clear signal intensity in the test line over the threshold values in both visual Rann score and Camag score, established at 2 units and 50 units respectively (FIGS. 6B, 6C). The limit of detection of the lateral flow immunoassay was 12 U/ml for visual and scanner analysis for both serum and blood samples.

The invention claimed is:

1. A lateral flow immunoassay device for the detection of anti-drug antibodies against infliximab (IFX) comprising:
   a membrane comprising:
   a capture area;
   sample application area;
   flow path from the sample application area to the capture area; and
   conjugate area located in the flow path, the conjugate area comprising a conjugate pad made of a bibulous, porous or fibrous material capable of absorbing liquid, the conjugate pad being mounted on the membrane such that the conjugate pad at least partially overlies the membrane,
   wherein the conjugate pad of the conjugate area comprises the IFX, which is detectably labeled with a label detectable by visual inspection, the conjugate pad further comprising a control molecule labeled with the same label detectable by visual inspection used to label the IFX, and
   wherein the capture area comprises a test line at a first position, which comprises the IFX, which is unlabeled, immobilized thereto, and further comprises a control line at a second position different from the first position, which comprises unlabeled anti-control molecule antibodies immobilized thereto,
   wherein the conjugate pad comprises a surface-active agent to reduce hydrophobicity of the material.

2. The lateral flow immunoassay device according to claim 1, wherein the membrane is a nitrocellulose membrane.

3. The lateral flow immunoassay device according to claim 1, wherein the label detectable by visual inspection comprises gold colloidal particles.

4. The lateral flow immunoassay device according to claim 1, wherein the sample application area comprises a blood separation pad.

5. The lateral flow immunoassay device according to claim 1, further comprising a distal absorbent pad.

6. The lateral flow immunoassay device according to claim 1, further comprising:
   a container in which the device is placed.

7. A method of detecting anti-drug antibodies against a biological drug in a biological sample from a patient, the method comprising:
   providing a lateral flow immunoassays device according to claim 1;
   applying the biological sample to the sample application area; and
   detecting anti-drug antibodies against a biological drug in the biological sample from the patient by visually detecting the label at the test line and at the control line,
   wherein the biological drug is IFX.

8. A method of modulating a biological drug treatment administered to a patient in need thereof, comprising the steps of:
   a) analyzing a biological sample using a lateral flow immunoassay device according to claim 1 to detect anti-drug antibodies against the biological drug; and
   b) modulating a next biological drug dose to be administered to the patient on the basis of a result obtained in step a),
   wherein the biological drug is IFX.

9. The method, according to claim 8, wherein the biological sample is whole blood or serum.

10. The method, according to claim 8, wherein in step a) the method measures trough levels of the anti-drug antibodies against IFX.

11. A method of predicting whether a patient will respond or not to a treatment with a first dose or a further dose of a biological drug comprising the steps of:
   a) analyzing a biological sample using a lateral flow immunoassay device according to claim 1 to detect anti-drug antibodies against the biological drug; and
   b) determining whether a patient will respond or not to a first dose or a further dose of a biological drug on the basis of the results obtained in step a),
   wherein the biological drug is IFX.

12. A method of determining whether a patient should receive a further dose of a biological drug comprising the steps of:
   a) analyzing a biological sample using a lateral flow immunoassay device according to claim 1 to detect anti-drug antibodies against the biological drug; and
   b) determining whether the patient should receive a further dose of the biological drug on the basis of the results obtained in step a),
   wherein the biological drug is IFX.

13. The lateral flow immunoassay device according to claim 1, wherein the labeled IFX and labeled control molecule are sprayed onto the conjugate pad and dried.

14. The lateral flow immunoassay device according to claim 1, wherein the labeled control molecule is present in the flow path.

15. A lateral flow immunoassay device for the detection of anti-drug antibodies against IFX comprising:
   a membrane comprising:
   a capture area;
   sample application area;
   flow path from the sample application area to the capture area; and
   conjugate area located in the flow path, the conjugate area comprising a conjugate pad made of a bibulous, porous or fibrous material capable of absorbing liquid, wherein the material is treated with a surface-active agent to reduce hydrophobicity of the material, the conjugate pad being mounted on the membrane such that the conjugate pad at least partially overlies the membrane,
   wherein the conjugate pad of the conjugate area comprises the IFX, which is detectably labeled with a label detectable by visual inspection, the conjugate pad further comprising a control molecule labeled with the same label detectable by visual inspection used to label the IFX, and
   wherein the capture area comprises a test line at a first position, which comprises the IFX, which is unlabeled, immobilized thereto, and further comprises a control line at a second position different from the first position, which comprises unlabeled anti-control molecule antibodies immobilized thereto.

* * * * *